United States Patent [19]

Green et al.

[11] Patent Number: 4,677,970
[45] Date of Patent: Jul. 7, 1987

[54] ORTHOPEDIC HEAT TRANSFER SYSTEM FOR ORTHOPEDIC CASTS

[76] Inventors: Carlos J. Green, Rte. 5, Box 161B, Covington, La. 70433; John L. Hirsius, 4620 Richland; Marshall K. Book, 3939 Houma Blvd., both of Metairie, La. 70002

[21] Appl. No.: 764,833
[22] Filed: Aug. 9, 1985
[51] Int. Cl.$^4$ .............................................. A61M 1/00
[52] U.S. Cl. ..................... 128/82.1; 128/402
[58] Field of Search ............... 128/82.1, 400, 402; 165/46

[56] References Cited

U.S. PATENT DOCUMENTS

| | | | |
|---|---|---|---|
| 3,683,902 | 8/1972 | Artemenko et al. | 128/82.1 X |
| 4,114,620 | 9/1978 | Moore et al. | 128/400 |
| 4,139,004 | 2/1979 | Gonzalez, Jr. | 128/82.1 |

Primary Examiner—Stephen F. Husar
Attorney, Agent, or Firm—C. Emmett Pugh

[57] ABSTRACT

An orthopedic heating or cooling system to be built into a cast or splint and bodily integrated with it as the cast is being applied to the patient. One or more individual units are used independently or in combination to form a flowing liquid system to heat or cool specific portions of the injured limb in a controlled fashion. The individual units include liquid carrying tubes held in a fixed, crossing pattern and integrated into the cast by means of an open mesh covering. Hot or cold fluid is pumped from a reservoir through one or more of the individual units in the desired sequence and amount and then expelled back into the temperature controlled or conditioned reservoir. In this fashion one may heat or cool the entire area under the cast or only specific sections, as desired, greatly increasing the comfort to the patient.

14 Claims, 5 Drawing Figures

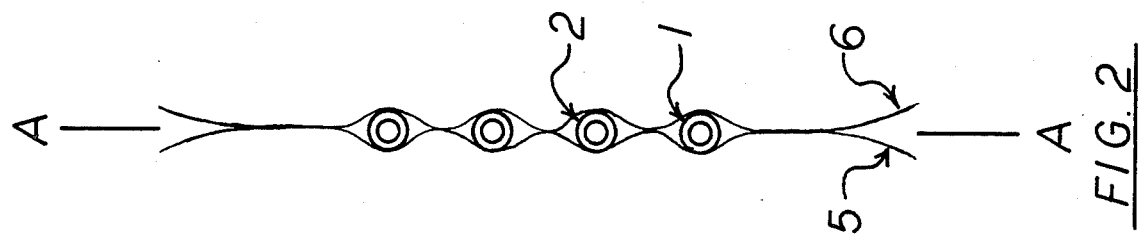
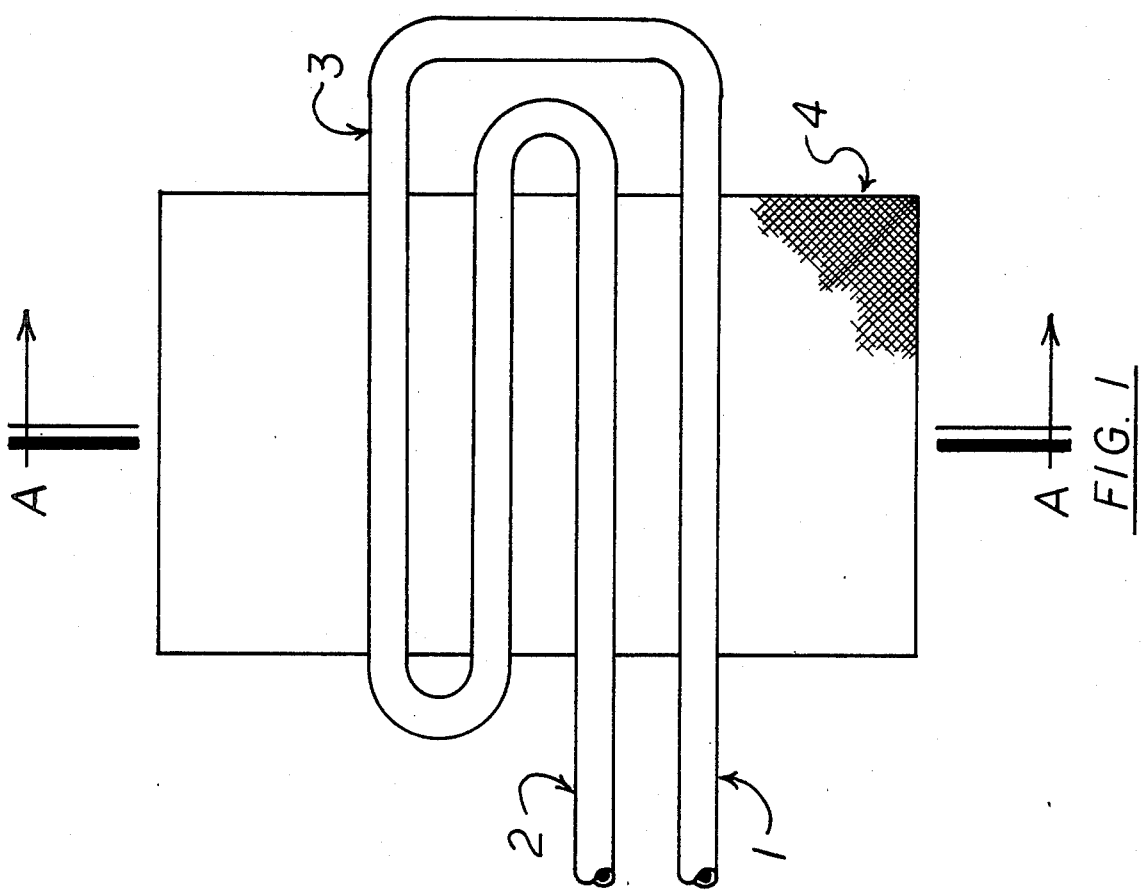

4,677,970

ORTHOPEDIC HEAT TRANSFER SYSTEM FOR ORTHOPEDIC CASTS

BACKGROUND OF INVENTION

1. Field of Invention

The present invention relates to an integral heating-/cooling system for use with orthopedic or surgical casts, braces or splints. More particularly, the present invention relates to fluid circulating system(s) to be built into a cast, brace or splint to regulate the temperature of the skin beneath such casts to, for example, alleviate pain or swelling.

2. Prior Art & General Background

U.S. Pat. No. 4,308,862 to Kalmar (issued Jan. 5, 1982) teaches the use of tubing in the construction of a plaster cast, but there are many fundamental differences between it and the present invention. For example, the tubes are used for ventilation and the tubing in the Kalmar patent is perforated, so that air in the tubing can escape into the cast. There is no closed system or return flow in the Kalmar device. The tubing is not divided into separable units to provide relief to specific areas. The Kalmar device is directed only to air ventilation of the area covered by the cast and not to controlled temperature regulation.

An article in the February 1956 issue of *Braces Today* entitled "Water-Cooled Body Casts Described" mentions the work of a Dr. Sullivan at the Mayo Clinic in November of 1955 in which apparently tubing was coiled around a cast prior to completion of the cast. Here again the objective was the overall cooling and general comfort of the patient, but not specific temperature control of selectable areas.

Additional prior patents which may be of interest are listed below:

| U.S. Pat. No. | Patentee(s) | Issue Date |
|---|---|---|
| 3,116,731 | T. E. Baxter | Jan. 7, 1964 |
| 3,656,477 | Thomas et al. | April 18, 1972 |
| 3,998,220 | Cleer, Jr. et al. | Dec. 21, 1976 |
| 4,076,019 | B. S. Sain | Feb. 28, 1978 |
| 4,235,228 | Gaylord, Jr. et al. | Nov. 25, 1980 |

The '731, '477 and '220 patents are directed to various types of air ventilating systems for orthopedic casts.

The '228 patent discloses the use of a padding layer and covering fabric of hydrophobic textile material in association with an orthopedic cast material, which acts to wick moisture from the skin of the wearer to the outer surface of the cast material. The evaporation of the moisture is claimed to alleviate skin irritation and odor beneath the cast.

The '019 patent includes the use of a felted layer of polyester or cotton fibers with ground silica-gel to absorb perspiration from the body, claiming to improve the patient's comfort.

Various heating pads of course are also known in which for example a heated liquid is passed through a disposable material which includes fluid passageways for the liquid to pass in and out of, an example being "Duo-Therm" disposable pad made by American Hospital Supply Corp. of Indianopolis, IN.

3. General Discussion of the Invention

Where there are surgioal incisions or fractures, there is an increase in swelling and clots, which can be reduced by application of ice or a cold pack. After surgery or fracture, however, a cast is usually applied to the affected area. This prevents the application of ice or a cold pack, because there is no ready way or means of applying ice or a cold pack to the affected area after the cast is applied. However, by means of the present invention, which is affixed to the inside of the cast at the time of lamination, and bodily integrated into the cast structure, the specific affected areas can be cooled (or warmed) at various desirable temperatures, thus reducing swelling and pain.

The present invention provides one or more sealed units of varying sizes and of lightweight but structurally sound construction. Each unit of the total system has an independent inlet port that accepts the hot or cold fluid for circulation throughout a number of for example "U" shaped passages, which form the individual units. The fluid is then expelled through an outlet port and either returned to the reservoir or channeled through the next individual unit in the system. Each unit is positioned inside the cast at a desired location to relieve swelling or pain.

The tubing is affixed to and sandwiched between preferably two opposing sheets of mesh material, the open interstices of the mesh allowing the unit to be bodily incorporated into the cast during the making of the cast.

BRIEF DESCRIPTION OF THE DRAWINGS

For a further understanding of the nature and objects of the present invention, reference should be had to the following detailed description, taken in conjunction with the accompanying drawings in which like parts are given like reference numerals and wherein:

FIG. 1 is a top view of the preferred embodiment of the liquid circulation insert for one unit of the present invention.

FIG. 2 is a sectional view taken along section lines A—A of FIG. 1.

DETAILED DESCRIPTION OF THE PREFERRED EXEMPLARY EMBODIMENT(S)

Figure 3:
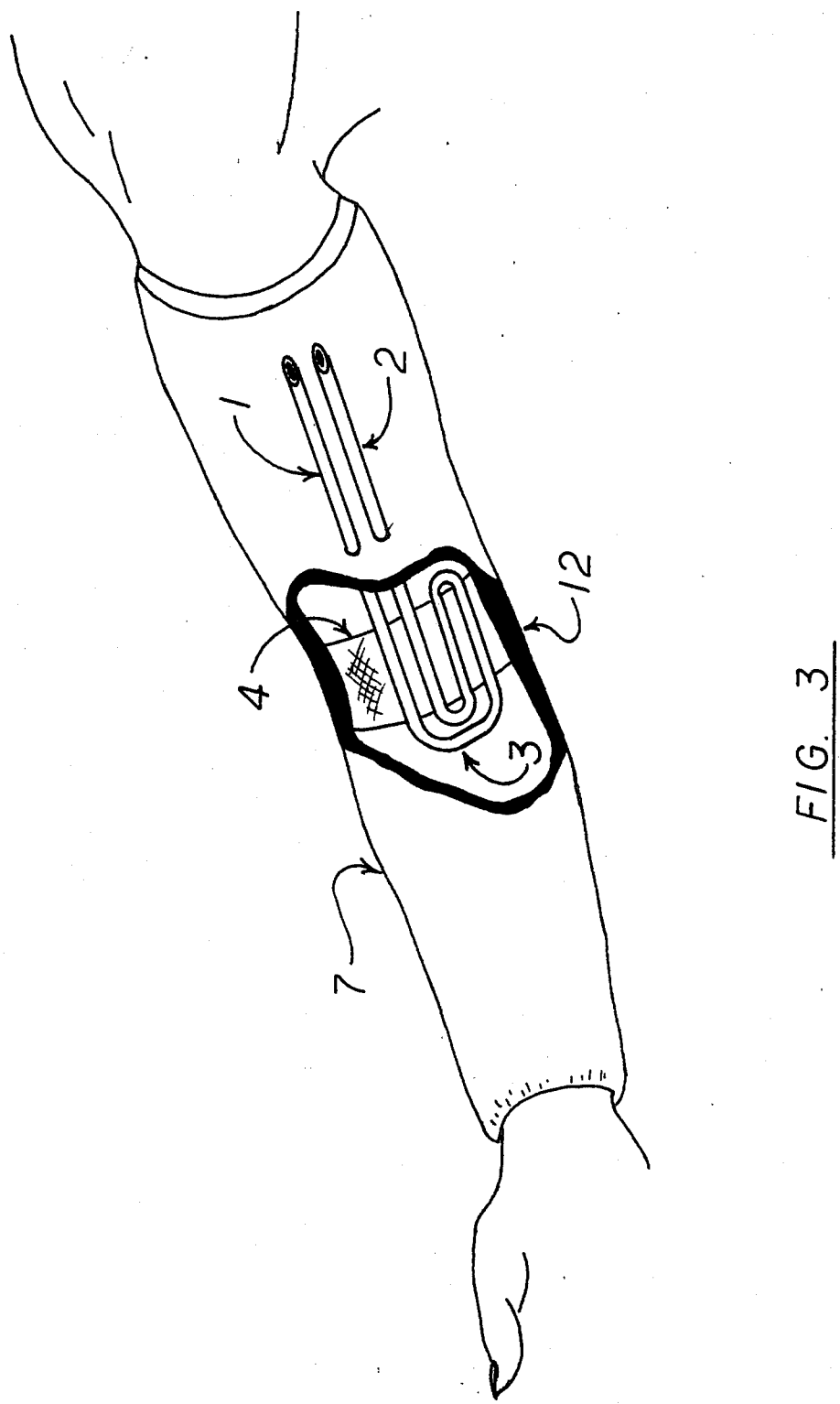
FIG. 3 is a side view of an arm cast, partially cutaway, showing a single unit in position.

A single unit of the preferred embodiment of the liquid circulation insert used in the present invention is shown in FIG. 1. The unit includes a flexible tubing 3 of suitable size and material for the effective transfer of heat, one exemplary size being seven thirty-seconds (7/32") of an inch (5.55 mm) in outside diameter with one thirty-seconds (1/32") of an inch (0.79 mm) wall thickness, an exemplary suitable material being "Tygon" or other similar material. A specific exemplary tubing would be "Tygon R-3603," which has a maximum recommended operating temperature of one hundred and sixty-five degrees Fahrenheit (165° F.; 74° C.).

The flexible tubing 3 is preferrably positioned in the squared off, "U" shaped coil pattern shown in FIG. 1 or in some similar pattern yielding a high degree of surface contact or interfacing between the tubing 3 and the patient's skin. This positioning provides a substantial amount of effective heat transfer area between the liquid flowing from the reservoir 11 (note FIG. 4) and the area of the patient's trauma or contusion injury.

With the tubing 3 positioned in its proper pattern, it is then restrained so that it remains in a flat configuration by means of securing mesh sheets 4. The mesh 4 of the preferred embodiment can be made of a nylon weave or open netting or other similar material which can be joined together to form a sandwiching sleave for the tubing 3 and can be secured to and integrated with the interior of the cast by means of the paster cast material flowing into the interstices of the mesh.

The mesh 4 is comprised of two independent halves or sheets 5 and 6 (note FIG. 2), which are secured together to hold the tubing 3 in position. The tubing 3 and mesh sheets 5, 6 may be affixed together simply by for example heating them, causing them to become fused together as a unit. The mesh 4 also provides the means for securing the unit to the cast and maintaining the proper desired relative positioning of the units in relation to each other and in relation to the affected area(s) needing treatment.

The tubing 3 and the securing mesh 4 thus form a single unit, which is later incorporated into a cast in accordance with the techniques of the present invention. In use the unit is placed at the desired position relative to the affected area needing treatment and as close as reasonably possible to the skin of the patient.

The standard plaster and cloth of the cast are then applied to the patient in the same manner as they would have been prior to the present invention. In this manner the unit or units are incorporated into the cast by the plaster material flowing into the mesh and are located in close proximity to the patient's injury in order to provide effective heat transfer.

Each unit has one inlet port 2 and one outlet port 1 for the continuous, closed passage of liquid into and out of the individual units.

An individual unit 12 in position inside an arm cast 7 is shown in FIG. 3. The inlet and outlet ports 1, 2 are shown as they extend outside of the cast to allow for the connection of the tubing 3 to and from the reservoir 11 and pump 13 (note FIG. 4).

Figure 4:
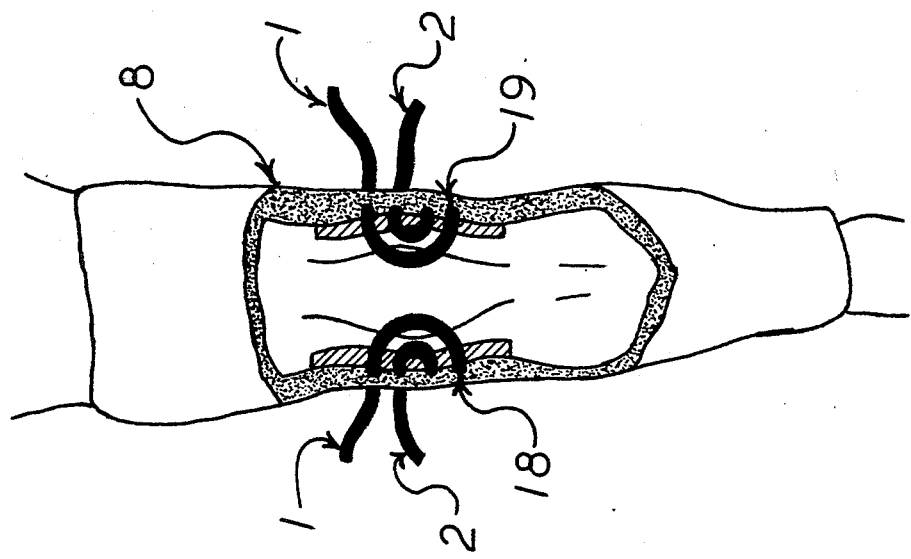
FIG. 4 is a schematic view of the general, over-all fluid circulation system using two interconnected units of the preferred embodiment of the insert in position in a leg cast to form a co-operative system.

A schematic representation of a complete system utilizing two independent but interconnected units 9 and 10, connected in series, is illustrated in FIG. 4. The pump 13 first draws a heated/cooled liquid from the reservoir 11 via the connecting tubing 17. Next, the first unit 9 receives the heated/cooled liquid via the input tubing 14 from the pump 13. The second unit 10 then serially receives the fluid via the connecting tubing 15. The fluid is then returned to the reservoir 11 via the output tubing 16.

Although heating fluids can be used, most contemplated uses of the present invention would be for a cooling fluid, such as for example ice water or the like. Also, the unit(s) can be used as the initial layer directly on the patient's skin in making up the cast. However, even in use as the initial layer, the plaster flows into the open mesh material and integrates the unit(s) into the cast.

The entire system could of course be run in the opposite flow direction, where a negative pressure in the units 9 and 10 is created by the pump 13, thereby causing liquid to be drawn up into the units 9 and 10 from the reservoir 11. The liquid would then be drawn out of the units 9 and 10 by the pump 13 and returned to the reservoir 11 via tubing 17.

The reservoir 11 stores the fluid and by suitable cooling or heating means maintains the liquid at or around its proper therapeutic temperature.

Figure 5:
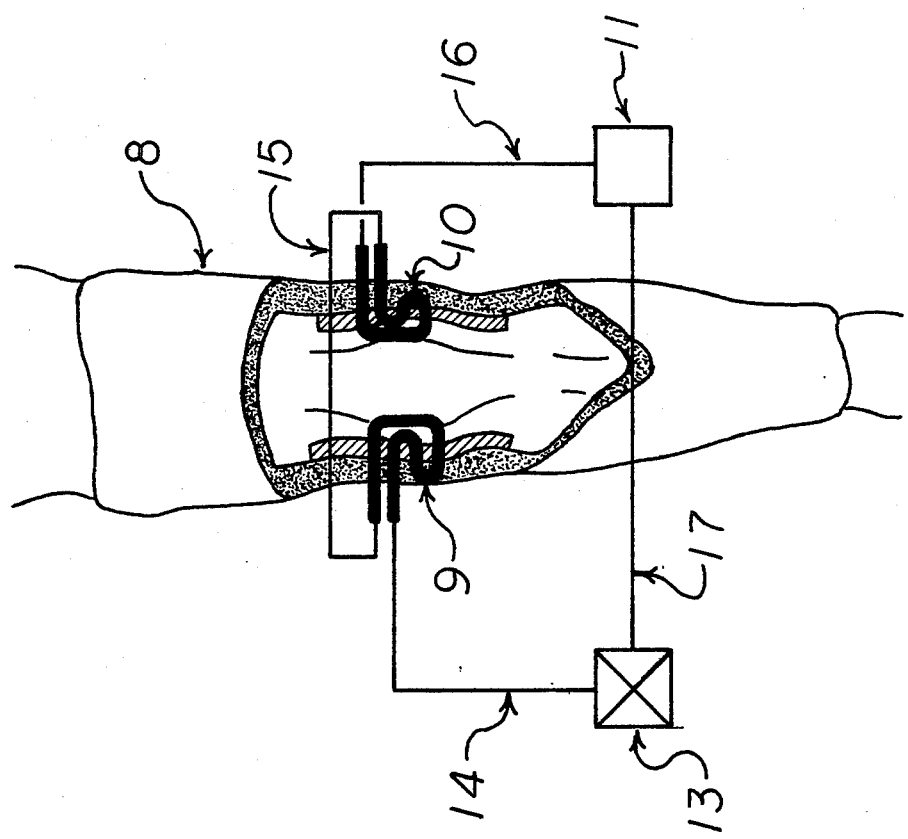
FIG. 5 is a front view, with the cast partially cutaway, showing the use of two independent units of the preferred embodiment integrated into the leg cast.

Several units located in the same cast may also be operated independently of each other, as illustrated in FIG. 5. The two independent units 18 and 19 are shown in position in a leg cast 8. These units are not interconnected in that the separate input and output ports 1, 2 of each are not connected to the other unit. Each unit is separately filled with cold or warm liquid as desired.

It should be noted that the present invention is applicable to splints and braces, as well as casts, and the term "casts" as generally used herein should be considered generic to include splints and braces as well. Likewise, the phrase "heat transfer" generically covers both a cooling as well as a heating treatment.

Because many varying and different embodiments may be made within the scope of the inventive concept herein taught, and because many modifications may be made in the embodiment(s) herein detailed in accordance with the descriptive requirements of the law, it is to be understood that the details herein are to be interpreted as illustrative and not in a limiting sense.

What is claimed is:

1. An orthopedic cast system using a liquid for the transfer of heat to or from a trauma location existing on an individual, comprising:
   continuous, closed, tubular pathway means for circulation of a liquid medium into and out of a cast without fluid loss;
   restraining means associated with said tubular means for holding said tubular means in a fixed configuration at a fixed location;
   an inlet port allowing the liquid medium into said tubular means;
   an outlet port allowing the removal of the liquid from said tubular means; and
   cast means surrounding and integrally incorporating said pathway means and said restraining means into the cast.

2. The method of forming a comforting orthopedic cast about a patient's injury, comprising the following steps:
   (a) providing at least one heat transferring unit located in juxtaposition to the injured area, said unit having a liquid containing, closed, continuous tubular pathway and at least one sheet of open mesh material to which the tubular pathway is affixed;
   (b) applying said unit and the cast making material to the injured area of the patient with the cast making material flowing into the interstices of the open mesh material, integrating said unit into said cast; and
   (c) flowing a temperature conditioned liquid through said closed tubular pathway, causing heat to be transferred between the injured area of the patient and the temperature conditioned liquid, producing therapeutic results.

3. An orthopedic system of selectively heating or cooling desired portions of an area covered by a rigid, orthopedic cast or other immobilizing device, which restricts between the skin and the air, comprising:
   a hard, rigid layer positionable adjacent to the body to immobilize a portion of the patient and having an outer layer on its side opposite to the patient's body;
   at least one heat transferring unit located between the outer surface of said layer and the patient's body and held in place by said rigid layer in juxtaposition to the area to be cooled or heated;

a liquid containing, closed, continuous pathway means located in said heat transferring unit for the circulation of an operative heat transferring liquid medium;

reservoir means connected to said pathway means for storage and temperature conditioning of the operative heat transferring liquid medium;

conditioning means associated with said reservoir means for conditioning the temperature of the heat transferring liquid medium; and pump means associated with said reservoir for supplying the necessary motive force for circulation of the heat transferring liquid medium through said pathway means.

4. The system of claim 3, wherein there is included a multiple number of said heat transferring units.

5. The system of claim 4, wherein the pathway means of said units are serially connected, the liquid medium flowing from the reservoir into one unit and then into the next one sequentially until the liquid medium returns to said reservoir.

6. The system of claim 4, wherein the temperature of the liquid medium flowing through at least one of said units is independent of the liquid medium flowing through at least one of the other units.

7. An orthopedic system of selectively heating or cooling desired portions of an area covered by a rigid, orthopedic cast which restricts contact between the skin and the air, comprising:

at least one heat transferring unit located in juxtaposition to the area to be cooled or heated;

a liquid containing, closed, continuous pathway means located in said heat transferring unit for the circulation of an operative heat transferring liquid medium;

reservoir means connected to said pathway means for storage and temperature conditioning of the operative heat transferring liquid medium;

conditioning means associated with said reservoir means for conditioning the temperature of the heat transferring liquid medium; and pump means associated with said reservoir for supplying the necessary motive force for circulation of the heat transferring liquid medium through said pathway means;

said pathway means further comprising at least one continuous tube forming a cross pattern; and wherein said unit further comprises:

at least one sheet of mesh material to which said tube is fixed, the cast material having flowed into said mesh material integrating said unit into the cast.

8. The system of claim 7, wherein there is included: two of said sheets of mesh material, one sheet located on one side of said tubing and the other located on the other side of said tubing, the tubing being sandwiched between said sheets of mesh material.

9. The system of claim 8, wherein said tubing and said sheets are of plastic material fused together.

10. The system of claim 7, wherein said tubing forms a series of adjacent "U" shaped, side-by-side sections located in common plane.

11. The system of claim 7, wherein said pathway includes only one single continuous tube forming a crossing pattern.

12. The system of claim 7, wherein there is included a multiple number of said heat transferring units.

13. The system of claim 12, wherein the pathway means of said units are serially connected, the liquid medium flowing from the reservoir into one unit and then into the next one sequentially until the liquid medium returns to said reservoir.

14. The system of claim 12, wherein the temperature of the liquid medium flowing through at least one of said units is independent of the liquid medium flowing through at least one of the other units.

* * * * *